United States Patent [19]

Karup et al.

[11] Patent Number: 5,405,857
[45] Date of Patent: Apr. 11, 1995

[54] 3-SUBSTITUTED 1,2,3,4,-OXATRIAZOLE-5-IMINE COMPOUNDS, A PROCESS FOR THE PREPARATION THEREOF AND A PHARMACEUTICAL PREPARATION CONTAINING SAID COMPOUNDS

[75] Inventors: Gunnar L. Karup, Copenhagen; Herbert F. Preikschat, Birkerod; Tim N. Corell, Lyngby; Bodil G. Lissau, Frederiksberg; Finn P. Clausen, Allerod; Soren B. Petersen, Hvidovre; Borge I. F. Alhede, Greve Strand, all of Denmark

[73] Assignee: A/S GEA Farmaceutisk Fabrik, Frederiksberg, Denmark

[21] Appl. No.: 90,012

[22] PCT Filed: Feb. 11, 1992

[86] PCT No.: PCT/DK92/00043
§ 371 Date: Jul. 19, 1993
§ 102(e) Date: Jul. 19, 1993

[87] PCT Pub. No.: WO92/13847
PCT Pub. Date: Aug. 20, 1992

[30] Foreign Application Priority Data

Feb. 12, 1991 [DK] Denmark ............................ 0238/91

[51] Int. Cl.$^6$ .................... C07D 273/00; A61K 31/41
[52] U.S. Cl. ................................... 514/361; 548/125; 546/277; 544/405; 514/252; 514/340
[58] Field of Search ............... 548/125; 514/361, 252, 514/340; 546/277; 544/405

[56] References Cited

U.S. PATENT DOCUMENTS 4,329,355 5/1982 Henry et al. .......................... 424/72

FOREIGN PATENT DOCUMENTS 45-20904 7/1970 Japan .
45-21102 7/1970 Japan .
2015878 9/1979 United Kingdom .

OTHER PUBLICATIONS

Chemical Abstracts, vol. 73, No. 17, Oct. 26, 1970, (Columbus, Ohio, U.S.), p. 361, Abstract No. 87922f, & JP,A, 7021102 (N-acyl-anhydro-1,2,3,4-oxatriazole-5-imines) Jul. 17, 1970.
Chemical Abstracts, vol. 73, No. 17, Oct. 26, 1970, (Columbus, Ohio, U.S.), p. 362, Abstract No. 87930g, & JP,A, 7020904 (Mesoionic compounds) Jul. 15, 1970.
Journal of Organic Chemistry, vol. 30, Feb. 1965, William G. Finnegan et al: "Synthesis And Reactions Of 1-Nitroso-1-Alkyl-2-Guanyl- and -2-Carbamylhydrazines", pp. 567–575.
Chemical Society, London, Journal Perkin transactions I, 1979, Robert N. Hanley et al: "Cyclic Mesoionic Compounds. Part 17. Synthesis, Spectroscopic Properties, and Chemistry of 1,2,3,4-Oxatriazolium-5-Aminides and 1,2,3,4-Tetrazolium-5-Olates", pp. 736–740.
Chemical Society, London, Journal Perkin transactions I, 1979, Robert N. Hanley et al: "Cyclic Meso-Ionic Compounds. Part 20. Mass Spectra of Meso-Ionic Heterocycles", pp. 747–751.
Acta Chemica Scandinavica, vol. 25, 1971 Carsten Christophersen et al: "The Reaction of 1-Substituted and 1,4-Disubstituted Thio-Semicarbazides with Nitrous Acid. 3-Substituted N-/5-(1,2,3,4-Oxatriazolo)-/Amides", pp. 625–630.
Chemical Pharm. Bull., vol. 19, No. 3, 1971 Katsutada Masuda et al: "Studies on Mesoionic Compounds. III. Synthesis of -3-Aryl-5-Imino-3,5-Dihydro-1-Oxa-2,3,4-Triazole Hydrochlorides and Their Derivatives", pp. 559–563.

*Primary Examiner*—Robert Gerstl
*Attorney, Agent, or Firm*—Oblon, Spivak, McClelland, Maier & Neustadt

[57] ABSTRACT

The present invention relates to hitherto unknown 3-substituted 1,2,3,4-oxatriazole-5-imine compounds which have proved to have biological effects making them suitable for treatment of cardiovascular diseases (blood clots), angina pectoris and asthma, a process for the preparation thereof and a pharmaceutical preparation comprising said compounds.

3 Claims, 2 Drawing Sheets

FIG. 1

3-SUBSTITUTED 1,2,3,4,-OXATRIAZOLE-5-IMINE COMPOUNDS, A PROCESS FOR THE PREPARATION THEREOF AND A PHARMACEUTICAL PREPARATION CONTAINING SAID COMPOUNDS

This application is a 371 of PcT/DK92/00043 Feb. 11.1992

1. Technical Field

The present invention relates to hitherto unknown 3-substituted 1,2,3,4-oxatriazole-5-imine compounds which have proved to have biological effects making them suitable for treatment of cardiovascular diseases (blood clots) and asthma, a process for the preparation thereof and a pharmaceutical preparation containing said compounds.

2. Background Art

K. Masuda et al., Chem. Pharm. Bull. 19 (3) pages 559–563 (1971) discloses 3-aryl-1,2,3,4-oxatriazole-5-imine compounds and acyl derivatives thereof, wherein the acyl group can be monosubstituted by methyl or halogen. Even though these compounds were synthesized in the hope of finding new hypotensive agents, no biological effects of the compounds are described.

C. Christophersen et al., Acta Chemica Scandinavica 25 pages 625–630 (1971), discloses 3-substituted 1,2,3,4-oxatriazole-5-imino compounds, where the 3-substituent can be propyl or phenyl or cyclohexyl. However, no biological effects of said compounds are described.

Hanley et al., J. C. S. Perkin Trans I, 736–740 (1979), discloses 3-aryl-1,2,3,4-oxatrizole-5-imine compounds, where the aryl group can be monosubstituted by methyl or halogen. However, no biological effects of the compounds are described.

The JP Patents Nos. 20904/70 and 21102/70 disclose 3-substituted 1,2,3,4-oxatriazole-5-imine salts and acyl derivatives thereof, wherein the 3-substituent can be aryl optionally monosubstituted by chloride or methyl. These compounds are stated to exhibit vasodepressor activity.

GB published specification number 2 015 878 discloses 3-phenyl-1,2,3,4-oxatriazole-5-imine compounds, for which a pesticidal and/or pest ovicidal and/or hebicidal activity has been found.

U.S. Pat. No. 4,329,355 discloses anhydro-5-imino-1,2,3,4-oxatriazolium hydroxides of a structure similar to the structure of the compounds of the present invention. However, the compounds known from this patent specification are only mentioned as being useful in the treatment of cancer.

Furthermore, from J. C. S. Perkin Trans I, 747–751 (1979) compounds of a structure similar to the structure of the compounds of the present invention are known. However, no biological effects of said compounds have been stated.

DISCLOSURE OF THE INVENTION

The present invention relates to hitherto unknown 3-substituted 1,2,3,4-oxatriazole-5-imine compounds of the general formula I and acid addition salts thereof wherein $R^1$ is the same or different alkyl or alkoxy groups having 1 to 3 carbon atoms, halogen, trifluoromethyl, nitro, cyano, phenyl or alkylsulphonyl groups, n is 1 to 5, and $R^2$ is hydrogen or a group of the formula II $$-X-Y-Q-(Z)_m \qquad \text{II}$$

wherein X is —C(O)—, —C(O)O—, —C(O)NH—, —S(O)$_2$ or a direct bond, Y is an alkylene group having 1 to 4 carbon atoms or a direct bond, and Q is alkyl, cycloalkyl, alkoxy or a phenyl, pyridyl, furanyl, thienyl, or pyrazinyl group being optionally substituted by Z, where Z is alkyl or alkoxy groups having 1 to 3 carbon atoms, halogen, hydroxy, acyloxy, trifluoromethyl, nitro, cyano or alkylsulphonyl, and m is 1 to 3, whereby Z also, when X is —C(O)—or —C(O)NH—, Y is a direct bond, and Q is substituted phenyl, can mean the structure I, wherein $R^2$ has the same meaning with respect to X, Y, and Q with the proviso that $R^2$ is not hydrogen, alkyl, benzoyl, trifluoroacetyl or an optionally substituted phenyl group, when $R^1$ is methyl or chlorine and n is 1, and $R^2$ is not hydrogen or an optionally substituted phenyl group, when $R^1$ is nitro, alkoxy, fluorine or bromine, and n is 1.

These compounds differ from the above known compounds by their chemical constitution, as they have a different substitution in the 3-position and/or in the 5-position of the oxatriazole ring, and they differ from the compounds known from the above patents by their biological effect, as they inhibit the blood platelet aggregation and have relaxation effect on trachea.

Accordingly, the invention also relates to a pharmaceutical preparation characterized by comprising as an active ingredient a compound of the formula I in association with a pharmaceutically acceptable carrier or diluent.

According to the invention the preferred compounds are the compounds of the general formula I, wherein n is 2 to 4.

In the general formula II Q preferably means alkyl and alkoxy groups having 1 to 6 carbon atoms.

The compounds of the invention can form acid addition salts with organic or inorganic acids. Suitable acids are for instance hydrogen chloride, hydrogen bromide, phosphoric acid, nitric acid, sulphuric acid, oxalic acid, lactic acid, tartaric acid, acetic acid, salicylic acid, benzoic acid, formic acid, propionic acid, pivalic acid, malonic acid, succinic acid, pimelic acid, fumaric acid, maleic acid, malic acid, sulfamic acid, phenylpropionic acid, gluconic acid, ascorbic acid, isonicotinic acid, methanesulphonic acid, p-toluenesulphonic acid, citric acid or adipic acid.

Moreover, the present invention relates to a process for the preparation of the 3-substituted 1,2,3,4-oxatriazole-5-imine compounds of the general formula I and acid addition salts thereof according to the invention, said process being characterized by a) ring closing a 1-arylthiosemicarbazide derivative of the general formula III wherein R[1] has the same meaning as in formula I, and R[3] is either H or a group of the formula IV

IV wherein X is a direct bond, and Y and Q—(Z)$_m$ have the same meaning as in formula I, by treatment with alkyl nitrite having 1 to 6 carbon atoms or alkali metal nitrite under acidic conditions at approximately 0° to 10° C., whereafter the resulting salt is optionally converted into the free compound and, if desired, is subjected to an acylation.

The process using of alkylnitrite having 1 to 6 carbon atoms is new and is preferred for the preparation of the compounds according to the invention, as a quantitative yield prior to purification is obtained hereby.

By the process according to the invention it is preferred to use ethyl nitrite as alkyl nitrite having 1 to 6 carbon atoms, and sodium nitrite as alkali metal nitrite.

It is known per se to cyclizise 1,4-disubstituted thiosemicarbazides with nitrous acid (sodium nitrite and acid) to form 3-substituted 1,2,3,4-oxatriazole-5-imines. The yields at this reaction are stated to be between 18 and 57%.

For reacting 1 equivalent of the 1-aryl-thiosemicarbazide derivative with alkyl nitrite having 1 to 6 carbon atoms, it is preferred to use 2 to 2.5 equivalents of alkyl nitrite in a suitable solvent, such as alkyl alcohol having 1 to 6 carbon atoms, to obtain 3-arylsubstituted 1,2,3,4-oxatriazole-5-imine salt in a substantially quantitative yield. After filtration of the precipitated sulphur and evaporation of the solvent, the product is, if necessary, recrystallized from for instance alkyl alcohol having 1 to 6 carbon atoms, acetonitrile or nitromethane, whereby the yields of the pure product obtained are usually between 60 and 95%.

Methanol or ethanol is preferably used as alkyl alcohol having 1 to 6 carbon atoms.

The preparation of the acylated compounds according to the invention is preferably carried out by dissolving a 3-aryl-1,2,3,4-oxatriazole-5-imine hydrochloride in a two-phase system comprising water and a halogenated hydrocarbon, preferably methylene chloride, to which the base quantities equivalent to the reaction, for instance sodium hydrogen carbonate and acylation agent, are added. The resulting product can be obtained by evaporation of the organic phase, and is optionally recrystallized from alkyl alcohol having 1 to 6 carbon atoms or acetonitrile. The yields of these compounds are usually in the range of 50 to 95%. Moreover, the acylated compounds according to the invention can be prepared in a manner known per se by reacting 3-aryl-1,2,3,4-oxatriazole-5-imine hydrochloride with an acylation agent in pyridine.

Suitable acylation agents are for instance: halogen formic acid esters, acid chlorides, anhydrides, O-alkyl and O-aryl esters, alkyl and aryl isocyanates, alkyl and aryl isothiocyanates.

The 5-iminoalkylated derivatives of 3-aryl-1,2,3,4-oxathiazole-5-imines according to the invention are preferably prepared from 1-aryl-4-substituted thiosemicarbazides by means of the process according to the invention using $C_1$-$C_6$-alkyl alcohol as solvent, preferably methanol or ethanol. The yields of these compounds are usually between 80 to 90%.

The acid addition salts usually result from the synthesis of the compounds of formula I, wherein R[2] is H, aryl, alkyl or cycloalkyl. The free compounds can be obtained from the acid addition salts in a manner known per se, that is for instance by dissolution or suspension in water and subsequent reaction with the base until an alkalic reaction (preferably at a pH value of 8.0 to 9.5), for instance with sodium hydrogen carbonate and subsequent isolation.

The necessary starting compounds of the general formula III can be prepared in a manner known per se. The starting compounds of formula III, wherein R[3] is H, can for instance be prepared by reacting the substituted arylhydrazine hydrochloride with an alkali thiocyanate or an ammonium thiocyanate in a suitable solvent, such as alcohol or water, during reflux for 6 to 18 hours, as described by for instance Houben-Weyl: "Methoden Der Organischen Chemie E4", page 513. The starting compounds of the general formula III, wherein R[3] is alkyl or aryl, can likewise be prepared in a manner known per se, for instance by reacting an aryl hydrazine with an alkyl or aryl thiocyanate in a suitable solvent, such as ether, methanol, ethanol, benzene or toluene, as described by Houben-Weyl: "Methoden Der Organischen Chemie E4", page 506.

PREPARATION OF THE STARTING MATERIALS

Preparation of 1 (3-chloro-2-methylphenyl)thiosemicarbazide 19.3 g (0.1 mole) of 3-chloro-2-methylphenylhydrazinehydrochloride were dissolved in 200 ml of absolute ethanol. 11.64 g (0.12 mole) of potassium thiocyanate were added to the solution, and the mixture was heated during reflux for 16 hours. The mixture was then cooled, whereby the product was partially precipitated, and the mixture was subsequently evaporated to dryness by means of a rotating evaporator. The product was recrystallized from 200 ml water and 250 ml methanol, separated by filtration and washed thoroughly with water.

Yield: 17.8 g=82.5% Melting point: 192°–193° C. Elemental analysis: $C_8H_{10}ClN_3S$: Calculated C: 44.54% H: 4.67% N: 19.48% S:14.86% Found C: 44.22% H: 4.58% N: 19.60% S:14.67% 500 MHz $^1H$ NMR (d$_6$-DMSO): δ9.33 (br s, 1H, NH), δ7.80 (br s, 1H, NH), δ7.72 (br s, 1H, NH), δ7.52 (br s, 1H, NH), δ6.80 (m, 3H, ArH), δ2.18 (s, 3H, CH$_3$).

Preparation of 1-(3-Chloro-2-methylphenyl)-4-(1-methylpropyl)thiosemicarbazide 1.44 g (10 mmole) of sec-butyl isothiocyanate were added to 1.56 g (10 mmole) of 3-chloro-2-methylphenyl hydrazine dissolved in 120 ml of toluene, and the mixture was refluxed for 2 hours and then evaporated. The remanence was stirred with a small amount of hexane, separated by filtration and dried.

Yield: 2.3 g=96.6% Melting point: 145°–146° C. Elemental analysis: Calc. C: 53.02% H: 6.67% N: 15.46% S:11.79% Cl:13.04% Found C: 53.22% H: 6.33% N: 15.52% S:11.84% Cl:13.02% 500 MHz $^1H$ NMR (CDCl$_3$): δ7.48 (s, 1H, NH), δ6.94 (m, 3H, ArH), δ6.90 (br s, 1H, NH), δ5.92 (s, 1H, NH), δ4.40 (m, 1H, CH), δ2.60 (s, 3H, CH$_3$), δ1.54 (m, 2H, CH$_2$), δ1.18 (d, 3H, CH$_3$), δ0.88 (t, 3H, CH$_3$).

EXAMPLE 1

3-(3-chloro-2-methylphenyl)-1,2,3,4-oxatriazole-5-imine hydrochloride 8.6 g (40 mmole) of 1-(3-chloro-2-methylphenyl)thiosemicarbazide were dissolved in 100 ml of methanol and 5 ml of 37% hydrochloric acid while being stirred at room temperature. The mixture was cooled to 0° to 5° C. by means of an ice bath, and then 6.3 g (7 ml) of ethyl nitrite was added in small quantities over a period of approximately 5 minutes. The mixture became dark coloured by the nitrous vapours, but turned light after a few minutes at the same time as free sulphur precipitated. The mixture was stirred for 10 minutes, and additional 0.9 g (1 ml) of ethyl nitrite was then added, and the reaction mixture was then left for about 20 minutes while being stirred. The sulphur was separated by filtration and the mixture was evaporated on a rotating evaporator at a bath temperature of 30° C. If necessary, the mixture was dehydrated by evaporation together with toluene/ethanol. The crystals were stirred with diethyl ether, separated by filtration and washed further with small amounts of diethyl ether.

Yield: 9.2 g=94% Melting point: 194°–195° C. (decomposes) IR: 1700 cm$^{-1}$. Elemental analysis C$_8$H$_7$ClN$_4$O, HCl, ¼ H$_2$O: Calculated C: 38.19% H: 3.41% N: 22.28% Cl:28.18% Found C: 38.07% H: 3.19% N: 22.30% Cl:28.58% 500 MHz $^1$H NMR (D$_2$O): δ7.52 (m, 3H, ArH), δ2.38 (s, 3H CH$_3$)

EXAMPLE 2 TO 28

The compounds shown in Table 1 were prepared in the same manner as described in Example 1.

EXAMPLE 29

3-(3-chloro-2-methylphenyl)-1,2,3,4-oxatriazole-5-imine 1.23 g (5 mmole) of the 3-(3-chloro-2-methylphenyl)-1,2 3,4-oxatrizole-5-imine hydrochloride prepared in Example 1 were dissolved in a two-phase system consisting of 30 ml of water and 10 ml of dichloromethane. The mixture was cooled in an ice bath to 5° C., and subsequently 0.84 g (10 mmole) of sodium hydrogen carbonate was carefully added in small quantities. After terminated development of carbon dioxide the mixture was stirred vigorously for about 10 minutes, whereafter the the organic phase was separated and evaporated.

Yield: 0.89 g=84.6% Melting point: 54°–56° C. Elemental analysis C$_8$H$_7$ClN$_4$O: Calculated C: 45.62% H: 3.35% N: 26.60% Cl:16.83% Found C: 45.95% H: 3.35% N: 26.30% Cl:17.27%

EXAMPLE 30

3-(3-trifluoromethylphenyl)-1,2,3,4-oxatriazole-5-(N-3-trifluoromethyl benzylcarbonyl)imine 2.66 g (10 mmole) of the 3-(3-trifluoromethylphenyl)-1,2,3,4-oxatriazole-5-imine hydrochloride prepared in Example 3 were dissolved in 45 ml water, and then 1.68 g (20 mmole) of sodium hydrogen carbonate was carefully added in small quantities. 20 ml of dichloromethane were added to the precipitated free base, which completely dissolved therein, and the mixture was cooled to 5° C. in an ice bath. 2.23 g (10 mmole) of 3-trifluoromethylbenzyl carboxylic acid chloride dissolved in 10 ml of methylene chloride was then added to the mixture while being vigorously stirred. The mixture was then stirred for 45 minutes, whereafter the organic phase was separated and washed twice with 30 ml wa-

TABLE 1

| Example | (R$^1$)$_n$ | Yield | Melting Point/°C. | IR(KBr)(cm$^{-1}$) | UV water$^a$/ ethanol$^b$ (nm) |
|---|---|---|---|---|---|
| 2 | 2-CF$_3$ | 71.8% | 162-164 | 1720(C—NH$^-$, HCl); 1320, 1300(CF$_3$) | 282$^a$ |
| 3 | 3-CF$_3$ | 81.8% | 170-172 | 1710(C—NH$^-$, HCl); 1330, 1300(CF$_3$) | 265$^b$ |
| 4 | 4-CF$_3$ | 55.6% | 182-184 | 1700(C—NH$^-$, HCl); 1330(CF$_3$) | |
| 7 | 3-CN | 96.2% | 199–200$^d$ | 2220(CN); 1750, 1700(C—NH$^-$, HCl) | |
| 8 | 4-CN | 59.4% | 190–191$^d$ | 2220(CN); 1700 (C—NH$^-$, HCl) | |
| 10 | 4-CH$_3$SO$_2$ | 71.2% | 193-195 | 1700(C—NH$^-$, HCl); 1290, 1150(SO$_2$) | |
| 11 | 2-CH$_3$, 3-CH$_3$ | 59.9% | 188-189 | 1700(C—NH$^-$, HCl) | 294$^a$ |
| 12 | 2-CH$_3$, 6-CH$_3$ | 55.8% | 173-174 | 1705(C—NH$^-$, HCl) | 279$^b$ |
| 13 | 2-CH$_3$, 4-Cl | 82.2% | 206–208$^d$ | 1745, 1700(C—NH$^-$, HCl); 1450, 1350(CH$_3$) | 300$^a$ |
| 14 | 2-CH$_3$, 5-Cl | 99.5% | 193–194$^d$ | 1740, 1700(C—NH$^-$, HCl); 1450, 1350(CH$_3$) | 288$^a$ |
| 15 | 4-CH$_3$, 3-Cl | 70.7% | 174-176 | 1700(C—NH$^-$, HCl); 1450, 1350(CH$_3$) | 292$^a$ |
| 16 | 2-CH$_3$, 3-F | 64.1% | 187-188 | 1730, 1700(C—NH$^-$, HCl) | 290$^a$ |
| 17 | 3-CF$_3$, 5-CF$_3$ | 67.8% | 187-188 | 1710(C—NH$^-$, HCl); 1330, 1310, 1285(CF$_3$) | |
| 18 | 3-CF$_3$, 4-Cl | 89.2% | 200-201 | 1740, 1700(C—NH$^-$, HCl); 1320, 1300(CF$_3$) | |
| 19 | 5-CF$_3$, 2-Cl | 82.9% | 195-197 | 1740, 1700(C—NH$^-$, HCl); 1320, 1300(CF$_3$) | 278$^a$ |
| 20 | 2-CH$_3$O, 5-Cl | 65.6% | 181-182 | 1710(C—NH$^-$, HCl); 1010(OCH$_3$) | |
| 21 | 2-Cl, 3-Cl | 47.6% | 163-164 | 1700(C—NH$^-$, HCl) | 290$^a$ |
| 22 | 2-Cl, 4-Cl | 70.8% | 178-180 | 1740, 1700(C—NH$^-$, HCl) | 296$^a$ |
| 23 | 2-Cl, 6-Cl | 77.3% | 122-125 | 1710(C—NH$^-$, HCl) | 288$^b$ |
| 24 | 3-Cl, 4-Cl | 78.7% | 183-184 | 1710(C—NH$^-$, HCl) | 291$^a$ |
| 25 | 3-Cl, 4-F | 93.5% | 192-193 | 1690(C—NH$^-$, HCl) | |
| 26 | 4-Cl, 2-F | 67.5% | 174-175 | 1710, 1690(C—NH$^-$, HCl) | 288$^a$ |
| 27 | 2-F, 3-F, 4-F | 93.5% | 174-175 | 1740, 1600(C—NH$^-$, HCl) | |
| 28 | 2,3,4,5,6-F | 40.1% | 142-143 | 1710(C—NH$^-$, HCl) | | ter. The methylene chloride was evaporated on a rotation evaporator, and the resulting substance was thoroughly stirred with diethyl ether, separated by filtration and dried.

Yield: 2.98 g=71.6% Melting point: 106°–108° C. IR: 1655 cm$^{-1}$, 1620–1590 cm$^{-1}$, 1350–1320 cm$^{-1}$. Elemental analysis $C_{17}H_{10}F_6N_4O_2$: Calculated C: 49.04% H: 2.42% N: 13.46% Found C: 48.87% H: 2.30% N: 13.59% 500 MHz $^1$H NMR (d$_6$-DMSO): δ8.02 ( m, 8H, ArH), δ3.88 (s, 2H, CH$_2$)

EXAMPLE 31 TO 45

The compounds shown in Table 2 were prepared as described in Example 30.

(CDCl$_3$): δ9.26 (d, 1H, J=1.5 Hz, ArH), δ8.56 (d, 1H, J=2.5 Hz, ArH), δ8.39 (dd, 1H, J=1.5 Hz and J=2.5 Hz, ArH), δ7.21 (m, 3H, ArH), δ2.58 (s, 3H, CH$_3$).

EXAMPLE 47

3-(2-chloro-3-chlorophenyl)-1,2,3,4-oxatriazole-5-(N-phenylcarbamoyl)imine 2.31 g (10 mmole) of the 3-(2-chloro-3-chlorophenyl)-1,2,3,4-oxatriazole-5-imine prepared in Example 21 were dissolved in 30 ml water, to which 0.9 g (10.7 mmole) of sodium hydrogen carbonate was added. After the development of carbon dioxide was terminated, 30 ml of dichloromethane and 1.20 g (10 mmole) of phenylisocyanate in 5 ml of dichloromethane were

TABLE 2

| Example | (R$^1$)$_n$ | R$_2$ | Yield | Melting Point/°C. | IR(KBr)cm$^{-1}$ | UV (ethanol (nm) |
|---|---|---|---|---|---|---|
| 31 | 3-CF$_3$ | CO$_2$C$_2$H$_5$ | 79% | 58–60$^d$ | 1710–1630(C—N—CO), (ester); 1330–1300(CF$_3$); 1210(ester) | |
| 32 | 3-CF$_3$ | COC$_6$H$_{11}$ | 30% | 98–101 | 2940, 2860(alif.); 1670, 1580 (C—N—CO); 1330–1300(CF$_3$) | |
| 33 | 3-CF$_3$ | SO$_2$—C$_6$H$_4$—4-CH$_3$ | 40% | 148–149 | 1680–1610, 1160(C—N—SO$_2$); 1320(CF$_3$) | |
| 34 | 3-CF$_3$ | 3-CO—C$_5$H$_4$N | 40% | 197–198 | 1650–1580(C—N—CO); 1350–1300(CF$_3$) | |
| 35 | 4-CF$_3$ | CO$_2$C$_2$H$_5$ | 54.3% | 162–165 | 1690–1620(C—N—CO), (ester); 1310–1290, (CF$_3$); 1210, 1175(ester) | |
| 36 | 2-CH$_3$, 3-Cl | COC$_6$H$_{11}$ | 91.5% | 128–130 | 2940, 2850(alif.); 1670, 1590(C—N—CO) | |
| 37 | 2-CH$_3$, 3-Cl | COC$_6$H$_4$—2-Cl | 73.4% | 155–156 | 1650, 1620(C—N—CO) | |
| 38 | 2-CH$_3$, 3-Cl | COC$_6$H$_4$—2-OCOCH$_3$ | 80% | 127–128 | 1770, 1220, 1190(ester); 1640, 1600–1570(C—N—CO) | |
| 39 | 2-CH$_3$, 3-Cl | 2-CO—C$_4$H$_3$O | 85.6% | 139–141 | 1640, 1590(C—N—CO) | 272 |
| 40 | 2-CH$_3$, 3-Cl | 2-CO—C$_4$H$_3$S | 87.8% | 148–150 | 1660, 1600(C—N—CO) | 272 |
| 41 | 4-CH$_3$, 3-Cl | CO$_2$C$_2$H$_5$ | 65.1% | 166–168 | 1710, 1685, 1640(C—N—CO), ester; 1210 (ester) | |
| 42 | 2-Cl, 3-Cl | COC$_6$H$_4$—3-NO$_2$ | 67.2% | 172–174 | 1660, 1590(C—N—CO); 1530, 1310(NO$_2$) | |
| 43 | 2-Cl, 4-Cl | 3-CO—C$_5$H$_4$N | 53.6% | 158–159 | 1660, 1580(C—N—CO) | |
| 44 | 3-Cl, 4-F | CO$_2$C$_2$H$_5$ | 79.8% | 176–178 | 2980(alif.); 1700, 1640(C—N—CO), (ester), 1210(ester) | |
| 45 | 2-F, 3-F, 4-F | CO$_2$C$_2$H$_5$ | 83% | 160–161$^d$ | 1775, 1710(C—N—CO), ester | |

EXAMPLE 46

3-(3-chloro-2-methylphenyl)-1,2,3,4-oxatriazole-5-(N-2-pyrazinoyl)-imine 2.47 g (10 mmole) of the 3-(3-chloro-2-methylphenyl)-1,2,3,4-oxatriazole-5-imine hydrochloride prepared in Example 1 were dissolved in 30 ml of water, to which 2.1 g (25 mmole) of sodium hydrogencarbonate were subsequently added while being stirred. After terminated development of carbon dioxide 30 ml of dichloromethane were added, whereafter the precipitated substance dissolved. 2.21 g (10 mmole) of pyrazine-2-carboxylic acid N-hydroxysuccinimide ester were then added. The mixure was left to stand while being heavily stirred for 16 hours, whereafter the methylene chloride phase was separated. This phase was washed twice with 30 ml water and evaporated. The substance was stirred with a small quantity of diethyl ether and separated by filtration.

Yield: 2.03 g=64.3% Melting point: 111°–112° C. Elemental analysis $C_{13}H_9ClN_5O$: Calculated C: 49.30% H: 2.86% N: 26.54% Cl:11.19% Found C: 49.10% H: 2.89% N: 26.37% Cl:11.40% 500 MHz $^1$H NMR added. The mixture was then heavily stirred for 30 minutes at room temperature, whereby the product partially precipitated. An additional 50 ml of dichloromethane and 30 ml of water were added, whereafter the phases separated. The dichloromethane phase was washed with 50 ml of water and evaporated. The recrystallization was performed in absolute ethanol.

Yield: 2.10 g=60.9% Melting point: 149°–151° C. Elemental analysis $C_{14}H_9Cl_2N_5O_2$: Calculated C: 48.02% H: 2.59% N: 20.01% Cl:20.25% Found C: 48.06% H: 2.67% N: 19.68% Cl:20.17% 500 MHz $^1$H NMR (CDCl$_3$): δ6.69 (m, 3H, ArH), δ7.58 (br s, 1H, NH), δ7.19 (m, 5H, ArH).

EXAMPLE 47a 3-(3-chloro-2-methylphenyl)-1,2,3,4-oxatriazole-5-(N-3,4-dimethoxyphenylethylcarbamoyl)imine 2.47 g (10 mmole) of the 3-(3-chloro-2-methylhenyl)-1,2,3,4-oxatriazole-5-imine hydrochloride prepared in Example 1 were dissolved in 30 ml water, to which 0.9 g (10.7 mmole) of sodium hydrogen carbonate was added. After the development of carbon dioxide was terminated, 30 ml of dichloromethane and 2.1 g (10 mmole) of homoveratrylisocyanate in 5 ml of dichloromethane were added. The mixture was then heavily stirred for 30 minutes at room temperature, whereafter the phases were separated. The methylene chloride phase was washed with water, filtrated and evaporated.

The substance was then washed with diethyl ether.
Yield: 3.60 g=86.12% Melting point: 148° to 151° C. IR: 1660 cm$^{-1}$ (N$^-$—CO—NH); 1260, 1030 cm$^{-1}$ (OCH$_3$) Elemental analysis $C_{19}H_{20}ClN_5O_4$: Calculated C: 54.61% H: 4.82% N: 16.76% Found C: 54.22% H: 4.67% N: 16.72%

EXAMPLE 48

3-(4-chloro-2-methylphenyl)-1,2,3,4-oxatriazole-5-(N-4-pyridinoyl)imine 0.90 g (5 mmole) of isonicotinic acid chloride was added to an ice-cooled suspension of 1.24 g (5 mmole) of the 3-(4-chloro-2-methylphenyl)-1,2,3,4-oxatriazole-5-imine hydrochloride prepared in Example 13 in 15 ml of pyridine.

The mixture was stirred a room temperature for an hour and 20 ml water were subsequently added (heat development). The mixture was cooled with ice and the substance was separated by filtration. The substance was then washed thoroughly with water and ether.

Yield: 1.35 g=85.52% Melting point: 180°-184° C. Elemental analysis $C_{14}H_{10}ClN_5O_2$: Calculated C: 53.36% H: 3.20% N: 22.13% Cl:11.23% Found C: 53.26% H: 3.19% N: 22.18% Cl: % 500 MHz $^1$H NMR (d$_6$-DMSO): δ8.77 (dd, 2H, PyrH, J=6 Hz, J=1.5 Hz), δ7.99 (dd, 2H, PyrH, H=6 Hz, J=1.5 Hz), δ7.77 (d, 1H, ArH, J=9 Hz), δ7.81 (d, 1H, Arh, J=2 Hz), δ7.71 (dd, 1H, Arh, J=9 Hz, J=2 Hz).

EXAMPLES 49 TO 59

The compounds shown in Table 3 were prepared in a manner described corresponding to that in Example 48.

TABLE 3

| Example | $(R^1)_n$ | $R_2$ | Yield | Melting Point/°C. | IR(KBr)(cm$^{-1}$) | UV (ethanol (nm) |
|---|---|---|---|---|---|---|
| 49 | 3-CF$_3$ | CO$_2$CH$_2$C$_6$H$_5$ | 30% | 136–137 | 1710, 1210(ester); 1630(C—N$^-$—CO); 1340–1310(CF$_3$) | |
| 50 | 3-CF$_3$ | 4-CO—C$_5$H$_4$N | 48% | 166–167 | 1670–1580(C—N$^-$—CO); 1350–1300(CF$_3$) | |
| 51 | 2-CH$_3$, 3-Cl | SO$_2$CH$_3$ | 86% | 166–167 | 1640, 1310, 1150(C—N$^-$—SO$_2$) | |
| 52 | 2-CH$_3$, 3-Cl | SO$_2$C$_6$H$_4$—CH$_3$ | 86.1% | 172–173 | 1670, 1630, 1320, 1170(C—N$^-$—SO$_2$) | |
| 53 | 2-CH$_3$, 3-Cl | COC$_6$H$_4$—4-OCH$_3$ | 98.3% | 122–123 | 1660, 1600(C—N$^-$—CO); 1250, 1010(OCH$_3$) | 273 |
| 54 | 2-CH$_3$, 3-Cl | 3-CO—C$_5$H$_4$N | 69% | 82–84 | 1660, 1680(C—N$^-$—CO) | |
| 55 | 2-CH$_3$, 3-Cl | 3-CO—C$_5$H$_3$N—5-Br | 92% | 149–160 | 1670–1580(C—N$^-$—CO) | |
| 56 | 2-CH$_3$, 3-Cl | 4-CO—C$_5$H$_4$N | 69.7% | 122–123 | 1660–1590(C—N$^-$—CO) | |
| 57 | 4-CH$_3$, 3-Cl | 3-CO—C$_5$H$_4$N | 36.3% | 142–144 | 1650, 1610, 1585(C—N$^-$—CO) | 279 |
| 58 | 2-CH$_3$O, 5-Cl | 4-CO—C$_5$H$_4$N | 50.2% | 157–168 | 1655, 1590(C—N$^-$—CO), 1010(OCH$_3$) | 269 |
| 59 | 2-CH$_3$O, 5-Cl | 2-CO—CH$_2$C$_4$H$_3$S | 46.9% | 89–91$^d$ | 1675, 1630(C—N$^-$—CO) | |

EXAMPLE 60

3-(3-chloro-2-methylphenyl)-1,2,3,4-oxatriazole-5-(N-1-methylpropyl)imine hydrochloride

1.5 g (20 mmole) of ethyl nitrite were added dropwise to an ice-cooled mixture of 2.16 g (8 mmole) of 1-(3-chloro-2-methylphenyl)-4-(1-methylpropyl)thiosemicarbazide and 2 ml of 37% hydrochloric acid in 80 ml ethanol over a period of 5 minutes. Shortly thereafter sulphur began to precipitate. The mixture was then stirred for an hour, whereafter the sulphur was filtered off and the mixture was evaporated. Ether (about 50 ml) was added and the substance slowly became crystalline. The crystals were separated by filtration and dried.

Yield: 2.00 g=93.73% Melting point: 151°–153° C. Elemental analysis $C_{12}H_{15}ClN_4O$, HCl, ¼ H$_2$O: Calculated C: 47.54% H: 5.32% N: 18.48% Cl:23.48% Found C: 46.91% H: 5.34% N: 18.17% Cl:23.45% 500 MHz $^1$H NMR (d$_6$-DMSO): δ7.84 (m, 3H, ArH), δ3.77 (m, 1H, CH), δ1.69 (m, 2H, CH$_2$), δ1.33 (d, 3H, CH$_3$), δ0.96 (t, 3H, CH$_3$)

EXAMPLE 62 To 63

The compounds shown in Table 4 were prepared in the manner described in Example 60.

TABLE 4

| Example | $(R^1)_n$ | $R_2$ | Yield | Melting Point/°C | IR(KBr)(cm$^{-1}$) |
|---|---|---|---|---|---|
| 62 | CH$_3$, 3-Cl | C$_6$H$_4$—4-CH$_3$, HCl | 84.3% | 150-160 | 1680(C—N⁻—C, HCl); 1460, 1380(alif.) |
| 63 | CH$_3$, 3-Cl | C$_6$H$_{11}$, HCl | 57% | 164-166 | 3000-2700(alif.); 1695(C—N⁻—C, HCl) |

EXAMPLE 64

3-(3-chloro-2-methylphenyl)-1,2,3,4-oxatriazole-5-(N-3-methoxypropyl)imine-hydrochloride 1.15 g (4 mmole) of 1-(3-chloro-2-methylphenyl)-4-(3-methoxypropyl)thiosemicarbazide were suspended in 40 ml of 96% ethanol and 1 ml of concentrated hydrochloric acid. The mixture was ice-cooled and a solution of 0.55 g (8 mmole) of sodium nitrite in 2 ml of water was dropwise added with the result that the suspension was thus dissolved and after a while the precipitation of sulphur began. The mixture was stirred again for one hour, and subsequently filtered clear. The mixture was evaporated at maximum 30° C., and 10 ml of ethanol followed by 50 ml ether were then added to the substance with the effect that the substance precipitated. The resulting product was separated by filtration and dried.

Yield: 1.0 g=78% Melting point: 133.1°-133.3.° C. IR (KBr) (cm$^{-1}$): 3000-2700 (aliphatic); 1710 (C—N⁻—C, HCl); 1085 (OCH$_3$).

EXAMPLE 65

3-(4-methylsuphonylphenyl)-1,2,3,4-oxatriazole-5-imine hydrochloride

A solution of 4.66 g (25 mmole) of 4-methylsulphonylphenyl hydrazinc in 100 ml of dry tetrahydrofuran was at 0° C. added to a solution of 1.32 g (12.5 mmole) of cyanogen bromide in 10 ml of ether. The mixture was stirred cold for an hour, and then separated by filtration and washed with dry ether. The filtrate was cooled to between −20° and −40° C., whereafter nitrogen oxide was added for about 45 minutes.

A surplus of ethanol/hydrochloric acid was then added to the mixture which was subsequently stirred at 5° C. for 4 hours. The resulting crystals were separated by filtration recrystallized by ethanol.

Yield: 1.20 g=35% Melting point: 193°-195° C. The IR and UV results are the same as those obtained by the product prepared in Example 10.

EXAMPLE 66

1,2-Bis(3-(3-chloro-2-methylphenyl)-1,2,3,4-oxatriazole-5-carbamoyl)benzene 4.94 g (20 mmole) of the 3-(3-chloro-2-methylphenyl)-1,2,3,4-oxatriazole-5-imine hydrochloride prepared in Example 1 were dissolved in 60 ml water, whereafter 3.78 g (45 mmole) of sodium hydrogen carbonate were added while being stirred. After terminated development of carbon dioxide 60 ml of dichloromethane were added, resulting in the precipitated substance dissolving. 2.13 g (10 mmole) of phthalylchloride were then added to the mixture. The mixture was left to stand while being stirred for 45 minutes at room temperature, whereafter the methylene chloride phase was separated. This phase was washed twice with 60 ml of water and then evaporated. The substance was stirred with a small quantity of diethyl ether and separated by filtration.

Yield: 3.53 g=64.1% Melting point: 176°-178° C. IR: 1685 cm$^{-1}$ broad. (C—N—CO) Elemental analysis C$_{24}$H$_{16}$Cl$_2$N$_2$O$_4$: Calculated C: 52.28% H: 2.93% N: 20.32% Cl:12.86% Found C: 51.87% H: 3.17% N: 20.02% Cl:12.55%

EXAMPLE 67

1,4-Bis(3-(3-chloro-2-methylphenyl)-1,2,3,4-oxatriazolyl-5-carbamoylamino)benzene 3.40 g (13.4 mmole) of the 3-(3-chloro-2-methylphenyl)-1,2,3,4-oxatriazole-5-imine hydrochloride prepared in Example 1 were dissolved in 50 ml of water, to which 2.25 g (26.8 mmole) of sodium hydrogen carbonate were subsequently added while the mixture was being stirred. After terminated development of carbon dioxide 50 ml of dichloromethane were added, resulting in the precipitated substance dissolving, and subsequently 1.1 g (6,9 mmole) of 1.4-phenylene diisocyanate in 20 ml of methylene chloride were added. The mixture was left to stand for 60 minutes while being stirred at room temperature, whereafter the methylene chloride phase was separated. This phase was then washed twice with 50 ml of water and evaporated. The substance was stirred with a small quantity of diethyl ether and separated by filtration.

Yield: 3.02 g=78.5% Melting point: 200°-201° C. dec. IR: 1660 cm$^{-1}$, (N—CO—NH) Elemental analysis C$_{24}$H$_{18}$Cl$_2$N$_{10}$O$_4$: Calculated C: 49.53% H: 3.12% N: 24.10% Cl:12.20% Found C: 49.52% H: 3.10% N: 23.33% Cl:12.50%

EXAMPLE 68

3-(3-chloro-2-methylphenyl)-1,2,3,4-oxatriazole-5-(N-1-adamantyl)imine hydrochloride 5.1.g (14.6 mmole) of 1-(3-chloro-2-methylphenyl)-4-(1-adamantyl)thiosemicarbazide were dissolved in 1.5 l of methanol and 1.5 ml of concentrated hydrochloric acid. The mixture was ice-cooled and 1.26 ml (30 mmole) of ethyl nitrite were added hereto, wherafter the mixture was stirred again for 2 hours at room temperature. The turbid solution was subsequently separated by filtration and evaporated. The substance crystallized after a few hours in the presence of diethyl ether admixed a small quantity of ethanol. The substance was filtered off and washed with ether.

Yield: 2.9 g=52.1% Melting point: 204.3° to 204.8° C. Elemental analysis $C_{18}H_{21}ClN_4O$, HCl: Calculated C: 56.79% H: 5.82% N: 14.69% Found C: 55.18% H: 5.80% N: 14.17% IR: 2910 cm$^{-1}$, 2860 cm$^{-1}$ (aliphatic); 1695 cm$^{-1}$ (C—N—C, HCl)

EXAMPLE 69

3-(3-chloro-2-methylphenyl)-1,2,3,4-oxatriazole-5-(N-3-hydroxyphenylcarbamoyl)imine 2.47 g (10 mmole) of the 3-(3-chloro-2-methylphenyl)-1,2,3,4-oxatriazole-5-imine hydrochloride prepared in Example 1 were dissolved in 30 ml of water, to which 0.9 g (10.7 mmole) of sodium hydrogen carbonate were subsequently added while being stirred. After terminated development of carbon dioxide 3-hydroxyphenylisocyanate in 30 ml of toluene was added while being stirred intensely. The mixture was then further stirred for 30 minutes with the result that a yellow substance precipitated. The substance was separated by filtration and washed twice with ethanol and once with diethyl ether.

Yield: 1.1 g=31.8% Melting point: 164° to 165° C. Elemental analysis $C_{15}H_{12}ClN_5O_3$: Calculated C: 52.11% H: 3.50% N: 20.26% Found C: 51.37% H: 3.42% N: 19.36% IR: 1630 cm$^{-1}$ (N—CO—NH), 1320 cm$^{-1}$, 1210 cm$^{-1}$ (Ar—OH)

PHARMACOLOGICAL TESTS

1. Inhibition of blood platelet aggregation

Compounds according to the invention were tested for their inhibition of clumping together (aggregation) of blood platelets (thrombocytes), which is the first phase of the formation of blood clots (thrombi). Such an inhibition may prevent the formation of blood clots and inhibit the development of new thrombi after a diagnosed thrombus.

The method of demonstrating this effect is a so-called aggregometer measurement, which was first described by Born (Nature (Lond.) 194, 927–929, 1962). Citrate stabilized (0.38% of sodium citrate, final concentration) venous blood from healthy testees is used, who have not used medicine for at least 8 days. Slight centrifugation (160×g for 10 minutes) results in PRP (blood plasma rich in platelets) which is pipetted. PPP (blood plasma poor in platelets) is obtained by an intense centrifugation (3000×g for 10 minutes) of the remaining blood. The light transmission is measured by the aggregometer (CHRONOLOG). PRP allows nearly no light transmitaaion, while PPP allows complete transmission of light. The PRP is placed in the aggregometer at 37° C. while being stirred by a magnet. Addition of a pro-aggregating substance causes the PRP to aggregate gradually and an increasing light transmission takes place at the same time. At complete aggregation a light transmission corresponding to PPP is obtained. Adnosine diphosphate (ADP) is used as pro-aggregating substance, said substance representing a basic biochemical mechanism for aggregation of blood platelets. The test substances are incubated for 3 minutes in PRP placed in the aggregometer at 37° C. during magnetic stirring. A predetermined positively aggregating dosage of adenosine diphosphate (ADP) (2 to 4 µM) is then added. At least 3 different concentrations of the test substances are tested to demonstrate dosage-dependent inhibition of the aggregation. A so-called $IC_{50}$-value (that is the concentration inhibiting the aggregation by 50% relative to the control aggregation) is calculated for each test substance by linear regression analysis (log concentration µM as constant ad abscissa and % inhibition as variable ad ordinate). The following known reference substances have been used: nitroglycerine (GTN), sodium nitroprusside (NNP) and SIN-1 (the active metabolite of molsidomine).

The results for eight compounds according to the invention and three reference substances appear from Table 5. It appears from Table 5 that the compounds according to the invention are substantially superior to the best reference substances. Nitroglycerine was inactive in this test.

TABLE 5
Inhibition of Blood platelet aggregation

| | $(R^1)_n$ | $R^2$ | $IC_{50}$ µM |
|---|---|---|---|
| GTN | | | 100 |
| NNP | | | 2.7 |
| SIN-1 | | | 3.9 |
| Example no. | | | |
| 7 | 3-cyano | H, HCl | 0.10 |
| 1 | 2-methyl, 3-chlor | H, HCl | 0.32 |
| 13 | 2-methyl, 4-chlor | H, HCl | 0.20 |
| 18 | 3-trifluormethyl, 4-chlor | H, HCl | 0.54 |
| 20 | 2-methoxy, 6-chlor | H, HCl | 0.18 |
| 34 | 3-trifluormethyl | nicotinoyl | 0.19 |
| 50 | 3-trifluormethyl | isonicotinoyl | 0.09 |
| 38 | 2-methyl, 3-chlor | acetylsalicyl | 0.20 |

2. Inhibition of plasminogen activator inhibitor (PAI) from blood platelets-(fibrinolytic activity)

Compounds according to the invention were tested for their inhibition of plasminogen activator inhibitor (PAI). An established thrombus comprises aggregated platelets cohered by fibrin. The organism has a fibrinolyric system for maintaining normal physiological conditions. Endogenous plasminogen is activated to plasmin (fibrinolysin, that is a proteolytic enzyme decomposing fibrin) by means of a tissue plasminogen activator (t-PA). The platelets include the enzyme PAI-1 inhibiting the activation of plasminogen to plasmin, and thus also the decomposition of fibrin.

A general stimulation of the fibrinolytic system can cause serious hemostatic side effects (haemorrhages). A specific inhibition of PAI-1 induces an increased fibrinolysis in areas with many platelets, which is exactly the case in thrombi. As a result a thrombolytic effect is obtained.

The method of demonstrating inhibition of PAI-1 is described by Lidbury et al. (Brit. J Pharmacol 101, 527–530, 1990). Human PRP prepared by slight centrifugation as previously mentioned is used, but at a low temperature (4° C.). By incubation of PRP (1 ml in a plastic tube) during a slight shaking at 37° C. the PAI-1 activity is liberated, said PAI-1 activity being measured spectrophotometrically by means of a two-step procedure using commercial kits (Spectrolyse TM /fibrin kit from BIOPOOL, Sweden).

The PAI-1 activity of the control PRP and PRP incubated with each of 6 compounds according to the invention and the reference substance sodium niroprusside (NNP) (50 μM of each for 60 minutes) appear from Table 6. The same Table also shows the percentage inhibition of PAI-1 activity compared to the control incubations.

It appears from Table 6 that the compounds according to the invention are all effective inhibitors of the PAI-1 liberazion from platelets. The potency is comparable with the potency of sodium nitroprusside (NNP).

TABLE 6

Inhibition of the PAI-1 activity

| Substance (50 μM) | PAI-1 activity (U/10⁸ platelets) | % Inhibition |
|---|---|---|
| Control | 3.24 | |
| Sodium nitroprusside NNP | 1.99 | 39 |
| Example No. | | |
| 8 | 1.83 | 44 |
| 24 | 2.14 | 34 |
| 20 | 2.09 | 35 |
| 12 | 2.04 | 37 |
| 18 | 1.93 | 40 |
| 1/29 (base) | 1.97 | 39 |

Stimulation of guanylate cyclase from blood platelets

Compounds according to the invention were tested for their stimulation of guanylate cyclase. The biological effect of NO (nitric oxide) in a plurality of cells (for instance platelets and polymorph nuclear leukocytes) is exercised through a stimulation of the enzyme, soluble guanylate cyclase. As a result cyclic guanosine monophosphate (c-GMP) is formed. The compounds according to the invention are all NO-donors. An increase of the cyclic guanosine monophosphate (c-GMP) in platelets results inter alia in a reduced aggregation ability and in a reduced ability to adhere to the walls of the blood vessels.

The method of demonstrating stimulation of guanylate cyclase is described by Axelsson and Andersson (European J. Pharmacol. 88, 71–79, 1983). Human platelets are homogenized and centrifugated in an ice-cold medium. The guanylate cyclase activity in the supernatant after incubation with and without the test substance for 15 minutes at 37° C. is measured by means of a radioimmuno assay (RIA) technique. The principle is that guanosine triphosphate (GTP) added in a constant quantity by means of guanylate cyclase is converted into cyclic guanosine monophosphate (c-GMP) which is determined by radioimmuno assay.

Eleven compounds according to the invention and the reference substances sodium nitroprusside (NNP) and SIN-1 have been tested in concentrations of 0.01 μM, 0.1 μM, 1.0 μM and 10 μM. A dose-dependent stimulation of the guanylate cyclase activity is shown for all of the compounds.

Table 7 shows the stimulation after 0.01 μM and 10 μM. The compounds according to the invention stimulate the guanylate cyclase activity already in the weakest concentration which is not the case with respect to sodium nitroprusside (NNP) and SIN-1.

TABLE 7

Stimulation of guanylate cyclase in platelets.

| Substance Concentration | Guanylate cyclase activity (pmole c-GMP/mg prot. × 15 minutes) | |
|---|---|---|
| | 0.01 μM | 10 μm |
| Sodium nitroprusside NNP | 0 | 3399 |
| SIN-1 | 0 | 59733 |
| Example 2 | 411 | 37920 |
| Example 8 | 897 | 64192 |
| Example 24 | 2374 | 59716 |
| Example 20 | 2225 | 47298 |
| Example 3 | 2499 | 47529 |
| Example 23 | 383 | 76915 |
| Example 1/29 (base) | 4407 | 61900 |
| Example 54 | 8139 | 18693 |
| Example 38 | 1024 | 82100 |
| Example 13 | 7642 | 48126 |
| Example 63 | 1761 | 72730 |

4. Relaxating effect on the trachea

Compounds according to the invention were tested for their ability to relax a pre-contracted trachea. A contraction of the respiratory passages in combination with a swelling of the mucuos membrane therein presents a vital factor at asthmatic conditions. Relaxation or dilation of the contracted respiratory passages will improve the asthmatic condition.

The method of demonstrating relaxation of a pre-contracted trachea is described by Emmerson & MacKay (J. Pharm. Pharmacol 31, 798, 1979). An isolated trachea from a guinea pig is used. After preparation of a strip which has maintained the circular musculature, the organ is divided into two parts of equal size. The two tracheal strips are suspended in their respective organ bath and connected to a transducer recording the contraction and relaxation of the organ by means of a recorder. The two tracheal strips are continuously bathed in a Krebs buffer at 37° C., constantly bubbled with carbogen (95% $O_2$ and 5% $CO_2$). After an equilibration time of about 3 hours the organs are tested for their sensitivity (contractility) to carbamylcholin a bolus being added directly to the bath (0.3 μM). If the contraction is satisfactory, the organs are transferred to the Krebs buffer containing the same concentration of carbamylcholine. The organs are now constantly exposed to the carbamylcholine and slowly develop a permanent contraction ("asthma"). The test substances are in bolus form added directly to the organ bath. After maximum effect (relaxation) the substances are removed by washing out and the tracheal strip reverts to its permanent contraction state. At least 3 different concentrations of the test substances are tested to demonstrate a dose-dependent relaxation of the organ. An $EC_{50}$-value (that is the concentration relaxing the organ by 50% relative to the maximum relaxation) is calculated for each test substance by means of a linear regression analysis (log concentration (μM) as a constant ad abscissa and % relaxation as variable ad ordinate). Sodium nitroprusside (NNP) and SIN-1 are used as reference substances.

The results for eight compounds according to the invention and for two reference substances appear from Table 8.

It appears from Table 8 that the compounds according to the invention are equipotent to NNP in relaxing pre-contracted tracheal strips and more potent than SIN-1. It should be underlined that the compounds according to the invention have a much more long-lasting effect compared to the reference substances.

TABLE 8

| Relaxation of the trachea | |
|---|---|
| Substance | EC$_{50}$ μM |
| Sodium nitroprusside (NNP) | 2.5 |
| SIN-1 | 18.3 |
| Example | |
| 53 | 0.7 |
| 20 | 2.7 |
| 12 | 4.9 |
| 1/29 (base) | 0.8 |
| 54 | 0.6 |
| 38 | 3.2 |
| 13 | 1.1 |
| 47a | 5.2 |

5. Inhibition of the leukocyte function

Compounds according to the invention were tested for their ability to increase the content of cyclic guanosine monophosphate (c-GMP), to inhibit the synthesis of the leukotriene B$_4$ (LTB$_4$), and to inhibit the chemotactical movement of polymorph nuclear leukocytes (PMN). The polymorph nuclear leukocytes play a vital part in the cellular part of the inflammation process. At diseases, such as asthma, the mucuos membrane of the respiratory passages is swollen as a result of an inflammation with a significant infiltration of polymorph nuclear leukocytes (PMN's) in particular. Particularly effective substances for the treatment of asthma are such which in addition to relaxing the musculature in the respiratory passages also have an anti-inflammatory effect on the cellular phase of the inflammatory process, that is inhibiting the leukocyte function.

The methods of demonstrating inhibition of the leukocyte function is described by Moilanen et al. (Abstracts, 2nd. International Symposium on Endothelium Derived Vasoactive Factors, Basel, 1992). Isolated human PMNs are incubated at 37° C. for 10 minutes, whereafter the content of cyclic guanosine monophosphate (c-GMP) is measured. Further, the synthesis of the LTB$_4$ is determined after stimulation with Ca-ionophore (A23187) and the chemotaxis (controlled movement) towards FMLP (a substance attracting the polymorph nuclear leukocytes, PMNs) is determined.

Three compounds according to the invention and the reference substance SIN-1 were tested for their ability to stimulate the content of cyclic guanosine monophosphate (c-GMP).

Table 9 shows a dose-dependant increase of the content of c-GMP in PMNs. The compounds according to the invention are all more potent than SIN-1.

The compounds according to the invention inhibited furthermore the leukotriene B$_4$ synthesis in the PMNs and the PMN chemotaxis towards the FMLP. SIN-1 was also able to inhibit these leukocyte functions, but only when used in higher concentrations.

Figure 1:
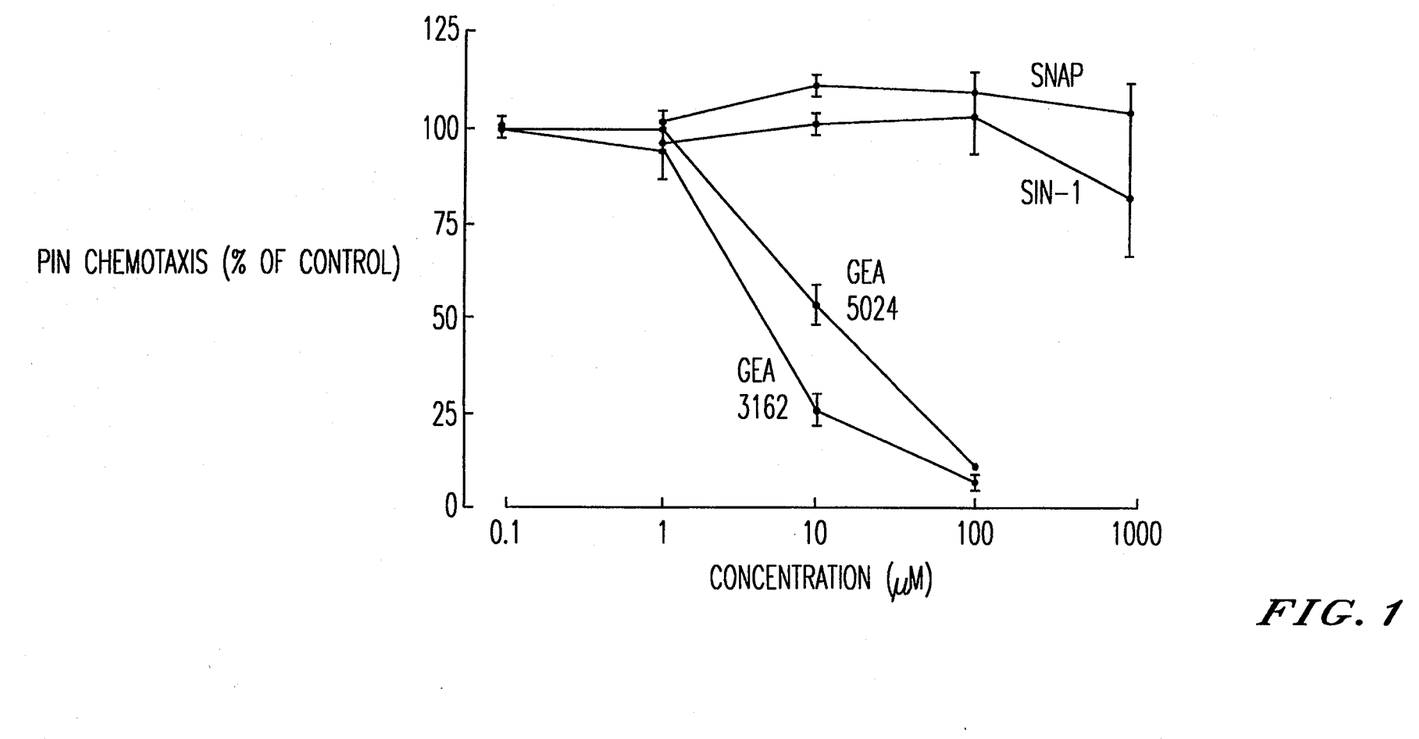
FIG. 1 illustrates the inhibition of the chemotaxis for 2 compounds according to the invention.
Figure 2A:
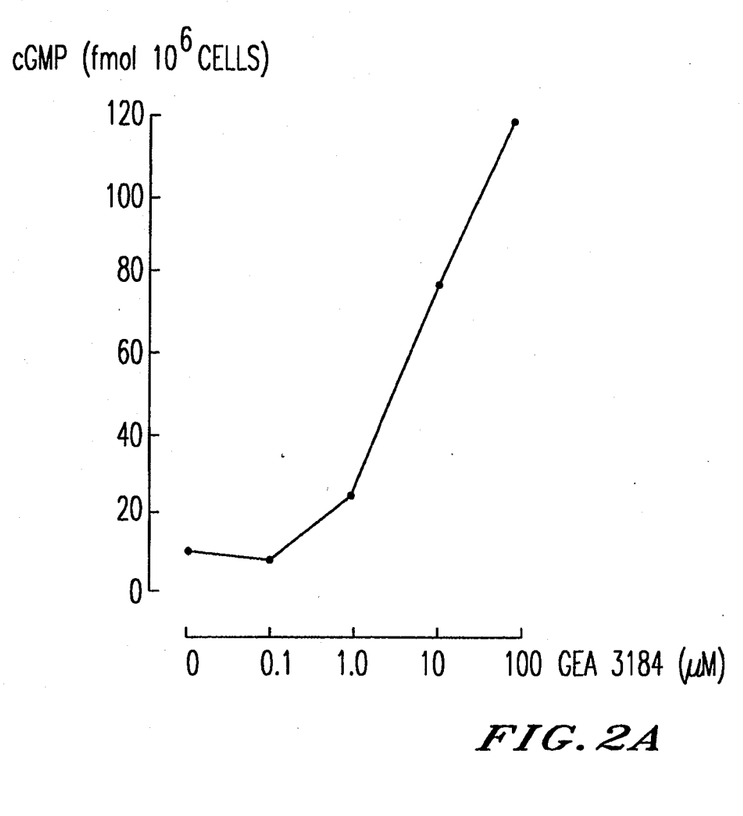
FIG. 2 illustrates the inhibition of the leukotriene B$_4$ synthesis compared to the increase of the content of c-GMP in the polymorph nuclear leukocytes (PMNs) for one compound according to the invention.
Figure 2B:
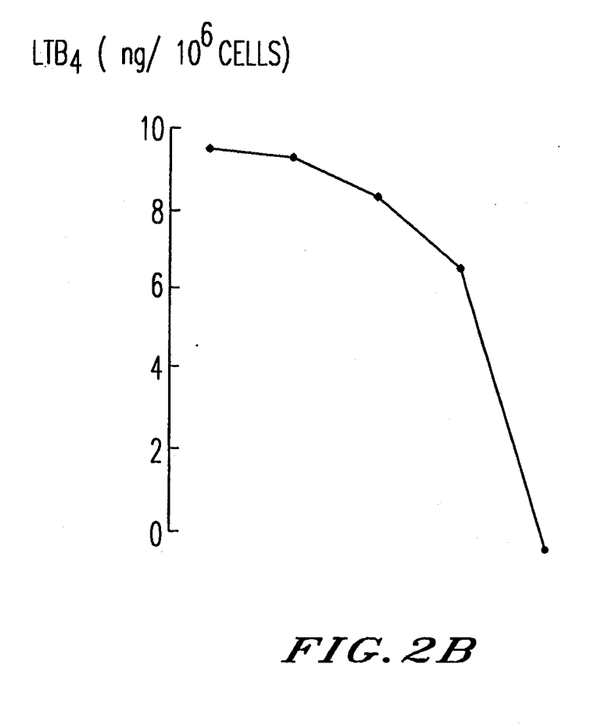

It appears that a parallel can be drawn between the increase in the cyclic guanosine monophosphate (c-GMP) and the decrease in the LTB$_4$ synthesis and the chemotactic movement of the PMNs.

TABLE 9

| Stimulation of c-GMP in PMNs | | |
|---|---|---|
| Substance | Concentration μM | c-GMP (fmole*/10$^6$ cells) |
| SIN-1 | 0 | 14 |
|  | 1 | 32 |
|  | 10 | 220 |
|  | 100 | 473 |
| Example 24 | 0 | 13 |
|  | 1 | 391 |
|  | 10 | 965 |
|  | 100 | 1078 |
| Example 20 | 0 | 13 |
|  | 1 | 175 |
|  | 10 | 492 |
|  | 100 | 866 |
| Example 1/29 (base) | 0 | 14 |
|  | 1 | 209 |
|  | 10 | 859 |
|  | 100 | 1044 |

*f = 10$^{-15}$

TOXICITY TESTS

Two tests were carried out on male rats, namely a determination of the "maximum tolerable dose" (MTD) and a test using multiple peroral doses. In addition, a LD$_{50}$ test was carried out intravenously on mice.

1. Determination of the maximum tolerable dose

In a MTD-test 10 animals were administered a dose of the substance once a day for a week, during which period the clinical and hematological parameters were recorded. When no signs of side effects appeared, the dose was increased in the following weeks until side effects appeared. The hemotological parameters measured were the following: the number of red and white blood cells, the number of blood platelets, the hemoglobin percentage, the hematocrit, and for the red blood cells also the average cell volume, the average cell hemoglobin content, and the average cell hemoglobin concentration. Furthermore, a differential count of the white blood cells was made.

The results of the test appear from Table 10.

TABLE 10

| Example | Dose mg/kg | Clinical observations* | Hematological parameters* | Increase in weight* |
|---|---|---|---|---|
| MTD study i.p. | | | | |
| 1 | 10 | N.R. | N.R | N.R. |
|  | 20 | CNS effect | increased neutrophilic granulocytes with toxic granulation | reduced |
| MTD study p.o. | | | | |
| 1 | 10 | N.R. | N.R. | N.R. |
|  | 20 | N.R. | N.R. | N.R. |
|  | 40 | N.R. | reduced RBC$^1$ reduced HGB$^2$ increased WBC$^3$ | N.R. |

*evaluated relative to the control group.
N.R.: nothing remarkable
$^1$red blood cells
$^2$hemoglobin percentage
$^3$white blood cells The compound prepared by the process of Example 1, administered intraperitoneally to rats, was tolerated with only minor side effects up to 20 mg/kg (~MTD). The most significant side effects at 20 mg/kg were a passing CNS effect, where the animals a few minutes after the administration seemed nervous and hyperactive, and where signs of a toxic reaction in the white blood picture (increased number of neutrophilic granulocytes and a toxic granulation in some cells). The corresponding value (MTD) using the same compound at peroral administration was 40 mg/kg. After administration of this dose signs of anemia and an increased content of white blood cells appeared after one week.

2. Peroral multiple dose administration

At this test the substances were administered perorally in a dose of 20 mg per kg. as solutions or suspensions once a day for 5 days to groups of 5 animals. Clinical observations were made every day and the above hematological parameters were measured on the third day of the test. The results appear from Table 11.

TABLE 11

| | | 5-day peroral administration | | |
|---|---|---|---|---|
| Example | Dose mg/kg | Clinical observations* | Hematological parameters* | Increase in weight* |
| 21 | 20 | N.R. | N.R. | N.R. |
| 26 | 20 | N.R. | N.R. | N.R. |
| 43 | 20 | N.R. | N.R. | N.R. |
| 38 | 20 | N.R. | N.R. | N.R. |
| 50 | 20 | N.R. | N.R. | N.R. |

*evaluated relative to the control group.
N.R.: nothing remarkable

At a dose of 20 mg/kg the compounds prepared in Examples 21, 26, 43, 38, and 50 caused no side effects in rats after administration for 5 days.

3. $LD_{50}$ test (According to Litchfield and Wileoxon, J. Pharmacol. Exp. Therap. 96, 99–113, 1949).

The intravenous $LD_{50}$-value was determined after one single injection of different doses of the compound prepared in Example 4.

The results appear from Table 12

TABLE 12

| Example | $LD_{50}$ mg/kg with male mice | 95% confindence limits female mice |
|---|---|---|
| 4 | 89 (82–97) | 81 (75–88) |

4. Pharmacological Conclusion

The compounds of the invention have pharmacological properties making them suitable for the treatment of thrombosis and asthma.

Thrombosis

The inhibition of the blood platelet aggregation together with the inhibition of PAI and the stimulation of c-GMP in platelets make the compounds interesting for the prevention of thrombosis as well as for dissolution of already established thrombi.

Asthma

The relaxation of the respiratory passages together with the inhibition of the leukocyte function make the compounds interesting for the treatment of asthma, whereby the latter property will inhibit the inflammatory swelling of the mucous membrane in the respiratory passages.

Beyond the pharmacological properties already mentioned the compounds of the invention also have a relaxing effect on other smooth muscle cells in for instance arteries, veins and cavernous tissue. Further, they decrease the blood pressure in rats.

The invention has been described with reference to preferred embodiments. Many modifications may, however, be carried out with out thereby deviating from the scope of the invention.

It is claimed:

1. A 3-substituted 1,2,3,4-oxatriazole-5-imine compound of Formula (I) or an addition salt thereof:

(I)

wherein $R^1$ is the same or different and is selected from the group consisting of $C_{1-3}$ alkyl, $C_{1-3}$ alkoxy, halogen, trifluoromethyl, nitro, cyano, phenyl and $C_{1-3}$ alkylsulphonyl, n is from 1–5 and $R^2$ is hydrogen or a group of the formula II $$X-Y-Q-(Z)_m \qquad (II)$$

wherein X is —C(O)—, —C(O)O—, —C(O)NH—, —S(O)$_2$ or a direct bond,

Y is a $C_{1-4}$ alkylene group or a direct bond, and

Q is a member selected from the group consisting of $C_{1-6}$ alkyl, $C_{3-6}$ cycloalkyl, $C_{1-6}$ alkoxy, phenyl, pyridyl, furanyl, thienyl and pyrazinyl, wherein Q may be optionally substituted by Z, wherein Z is a member selected from the group consisting of $C_{1-3}$ alkyl, $C_{1-3}$ alkoxy, halogen, hydroxy, acyloxy, trifluoromethyl, nitro, cyano and $C_{1-3}$ alkylsulphonyl, and m is from 1–3, whereby Z also, when X is —C(O)— or —C(O)NH—, Y is a direct bond, and Q is substituted phenyl, can mean the structure I, wherein $R^2$ has the same meaning with respect to X, Y and Q, with the proviso that $R^2$ is not hydrogen, alkyl, benzoyl or trifluoroacetyl, when $R^1$ is methyl or chlorine, and n is 1, $R^2$ is not hydrogen, when $R^1$ is nitro, alkoxy, fluorine or bromine, and n is 1, and $R^2$ is not an optionally substituted phenyl, pyridyl or $C_{1-6}$ alkyl.

2. A pharmaceutical composition comprising:

an effective amount of a compound according to claim 1 or a pharmaceutical acceptable salt thereof in association with a pharmaceutically acceptable carrier or diluent.

3. A method of treating cardiovascular diseases comprising:

administering to a patient in need thereof an effective amount of a compound of Formula (I) or a pharmaceutically acceptable salt thereof according to claim 1.

* * * * *